(12) United States Patent
Himeno et al.

(10) Patent No.: US 7,498,462 B2
(45) Date of Patent: Mar. 3, 2009

(54) PROCESS FOR PRODUCING α,β-UNSATURATED CARBOXYLIC ACID

(75) Inventors: Yoshiyuki Himeno, Hiroshima (JP); Akio Takeda, Hiroshima (JP); Seiichi Kawato, Hiroshima (JP); Wataru Ninomiya, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/588,921

(22) PCT Filed: Feb. 7, 2005

(86) PCT No.: PCT/JP2005/001748

§ 371 (c)(1),
(2), (4) Date: Aug. 9, 2006

(87) PCT Pub. No.: WO2005/080307

PCT Pub. Date: Sep. 1, 2005

(65) Prior Publication Data

US 2007/0142666 A1    Jun. 21, 2007

(30) Foreign Application Priority Data

Feb. 9, 2004  (JP)  ............ 2004-032170
Aug. 19, 2004 (JP)  ............ 2004-239429

(51) Int. Cl.
*C07C 57/04* (2006.01)
(52) U.S. Cl. .................... 562/512; 562/533
(58) Field of Classification Search ............ 562/512, 562/533
See application file for complete search history.

(56) References Cited

U.S. PATENT DOCUMENTS 4,147,884 A * 4/1979 Sheng et al. .......... 562/533

2002/0151747 A1 * 10/2002 Unruh et al. .......... 562/546
2007/0142666 A1    6/2007 Himeno et al.

FOREIGN PATENT DOCUMENTS

| JP | 48-32821 | 5/1973 |
| JP | 52-005707 | 1/1977 |
| JP | 52-17418 | 2/1977 |
| JP | 60-139341 | 7/1985 |
| JP | 60-139643 | 7/1985 |
| JP | 60-155148 | 8/1985 |
| WO | 02/083299 | 10/2002 |

OTHER PUBLICATIONS

T.Seiyama, N.Yamazoe, J-I.Hojo, M.Hayakawa☐☐Catalytic oxidation of olefins over metallic palladium suspended in water☐☐Journal of Catalysis, 24(1), Jan. 1972, 173-177.*
T.Seiyama, N.Yamazoe, J-I.Hojo, M.Hayakawa Catalytic oxidation of olefins over metallic palladium suspended in water Journal of Catalysis, 24(1), Jan. 1972, 173-177.*
Tetsuro, Seiyama et al., "Catalytic Oxidation of Olefins over Metallic Palladium suspended in water", Journal of Catalysis, vol. 24, No. 1, pp. 173-177, Jan. 1972.
U.S. Appl. No. 11/628,215, filed Dec. 1, 2006, Kawato, et al.
U.S. Appl. No. 11/719,461, filed May 16, 2007, Himeno, et al.
U.S. Appl. No. 12/159,396, filed Jun. 27, 2008, Himeno, et al.

* cited by examiner

*Primary Examiner*—Daniel M Sullivan
*Assistant Examiner*—Sudhakar Katakam
(74) *Attorney, Agent, or Firm*—Oblon, Spivak, McClelland, Maier & Neustadt, P.C.

(57) ABSTRACT

The object of the present invention is to provide a method for producing an α,β-unsaturated carboxylic acid in higher selectivity. The present invention resides in a method for producing an α,β-unsaturated carboxylic acid from an olefin or an α,β-unsaturated aldehyde in liquid phase by using a noble metal-containing catalyst and by causing a compound (A) having an acid dissociation exponent (pKa) of less than 4 to be present in the liquid phase.

12 Claims, No Drawings

PROCESS FOR PRODUCING α,β-UNSATURATED CARBOXYLIC ACID

TECHNICAL FIELD

The present invention relates to a method for producing an α,β-unsaturated carboxylic acid from an olefin or an α,β-unsaturated aldehyde by using a noble metal-containing catalyst.

BACKGROUND ART

There has been many researches on a method for producing an α,β-unsaturated carboxylic acid through liquid-phase oxidation of an olefin or an α,β-unsaturated aldehyde with molecular oxygen by using a noble metal-containing catalyst. For example, in Patent Documents 1 to 4, a method is disclosed, wherein an olefin is oxidized with molecular oxygen in liquid phase by using an activated supported palladium metal-containing catalyst which has been activated by contacting an olefin having carbon number of 3 to 6 with a supported palladium metal-containing catalyst. In particular, a method is disclosed, wherein a surfactant and an alcohol in Patent Document 2 and a free radical inhibitor in Patent Document 3 are caused to be present in each reaction system, respectively, to improve selectivity to an α,β-unsaturated carboxylic acid. In Patent Document 4, a method is disclosed, wherein a reaction solvent containing a carboxylic acid having carbon number of 2 to 6, tertiary butanol or a ketone having carbon number of 3 to 6 is used. Further, in Patent Documents 1 to 4, there are no descriptions concerning reaction solvents and additives having an acid dissociation exponent (pKa) of less than 4.

Patent Document 1: Japanese Patent Application Laid-Open No. 60-139,341.
Patent Document 2: Japanese Patent Application Laid-Open No. 60-139,643.
Patent Document 3: Japanese Patent Application Laid-Open No. 60-155,148.
Patent Document 4: International Publication No. WO 02/083,299.

DISCLOSURE OF INVENTION

1. Problem to be Solved by the Invention

However, when acrylic acid is produced from propylene by using the supported palladium metal-containing catalyst described in Examples of Patent Documents 1 to 4, by-products such as allyl acrylate and various polymers and oligomers are produced in large amount in addition to the by-products described in Patent Documents 1 to 4 (for example, acetaldehyde, acetone, acrolein, acetic acid and carbon dioxide). In Patent Documents 1 to 4, these polymers and oligomers are not captured, and hence, the actual selectivity to acrylic acid in view of these by-products is lower than those described in Examples of Patent Documents 1 to 4. Similarly, when methacrylic acid is produced from isobutylene, the selectivity to methacrylic acid becomes low because by-products such as methallyl methacrylate and various polymers and oligomers are produced in large amount. Further, with the increase in the concentration of acrylic acid or methacrylic acid to be produced, there is increase in the amount of acrylates or methacrylates which are by-products other than those above.

Consequently, the selectivity obtained in the method for producing an α,β-unsaturated carboxylic acid by using the catalyst described in Patent Documents 1 to 4 is not sufficient yet, and hence, a method in which an α,β-unsaturated carboxylic acid can be produced in higher selectivity has been desired.

2. Means for Solving Problem

The present invention resides in a method for producing an α,β-unsaturated carboxylic acid from an olefin or an α,β-unsaturated aldehyde in liquid phase by using a noble metal-containing catalyst and by causing a compound (A) having an acid dissociation exponent (pKa) of less than 4 to be present in the liquid phase.

The acid dissociation exponent (pKa) in the present invention means a logarithmic value of a reciprocal of a dissociation exponent of a compound (HA) in solution and the value at 25° C. in water solution at infinite dilution. More exactly, it is a value obtained from the following formula (2), in an acid dissociation-equilibrium reaction of HA represented by the following formula (1).

$$HA \rightleftarrows H^+ + A^- \tag{1}$$

$$pKa = -\log\frac{[H^+][A^-]}{[HA]} \tag{2}$$

Further, in the case that a compound has two or more stages of acid dissociation-equilibrium reactions, the acid dissociation exponent (pKa) of the compound means that in the first stage.

3. EFFECT OF THE INVENTION

By using a method for producing an α,β-unsaturated carboxylic acid from an olefin or an α,β-unsaturated aldehyde in liquid phase by using a noble metal-containing catalyst and by causing a compound (A) having an acid dissociation exponent (pKa) of less than 4 to be present in the liquid phase, it is possible to produce an α,β-unsaturated carboxylic acid in higher selectivity.

BEST MODE FOR CARRYING OUT THE INVENTION

In the present invention, when an α,β-unsaturated carboxylic acid is produced through liquid-phase oxidation of an olefin or an α,β-unsaturated aldehyde by using a noble metal-containing catalyst (hereinafter, sometimes expressed as "catalyst"), it is necessary to cause a compound (A) having an acid dissociation exponent (pKa) of less than 4 to be present in the liquid phase. The acid dissociation exponent (pKa) of the compound (A) is preferably 3 or less, more preferably 2 or less.

The amount of the compound (A) to be added is preferably such an amount that a concentration of the compound (A) in the reaction solution becomes 0.01% by mass to 30% by mass. It is more preferably 0.1% by mass or more, particularly preferably 0.5% by mass or more. Further, it is preferably 20% by mass or less, particularly preferably 15% by mass or less.

Examples of the compound (A) having an acid dissociation exponent (pKa) of less than 4 include inorganic compounds, organic compounds or chelating reagents, and among them, organic compounds are preferable and carboxylic acid compounds are more preferable. The carboxylic acid compounds may be aliphatic carboxylic acid compounds or aromatic carboxylic acid compounds; saturated carboxylic acid compounds or unsaturated carboxylic acid compounds; or mono-carboxylic acid compounds or polycarboxylic acid compounds such as dicarboxylic acid compounds. Further, as the carboxylic acid compounds, halogenated carboxylic acid compounds, nitrogen-containing carboxylic acid compounds such as amino acid compounds, keto acid compounds or oxy-acid compounds can be used.

Specifically, the examples include aspartic acid (pKa: 1.93), formic acid (pKa: 3.55), citric acid (pKa: 2.87), o-chlorobenzoic acid (pKa: 2.92), chloroacetic acid (pKa: 2.68), dichloroacetic acid (pKa: 1.30), trichloroacetic acid (pKa: 0.66), nicotinic acid (pKa: 2.05), lactic acid (pKa: 3.66), oxalic acid (pKa: 1.04), picric acid (pKa: 0.33), picolinic acid (pKa: 1.03), fluoroacetic acid (pKa: 2.59), difluoroacetic acid (pKa: 1.08), trifluoroacetic acid (pKa: 0.30), phthalic acid (pKa: 2.75), isophthalic acid (pKa: 3.50), terephthalic acid (pKa: 3.54), maleic acid (pKa: 1.75) and malonic acid (pKa: 2.65). Among them, any one of chloroacetic acid, dichloroacetic acid, trichloroacetic acid, fluoroacetic acid, difluoroacetic acid, trifluoroacetic acid, maleic acid and malonic acid is preferable, in particular, trifluoroacetic acid is preferable. The compound (A) can be used alone or in combination of two or more kinds.

The reason why the selectivity to an α,β-unsaturated carboxylic acid is improved by the addition of the compound (A) is not clear, however, the following reason is presumed. Firstly, the compound (A) is presumed to promote hydrolysis of an ester which is a by-product made from the reaction between the product α,β-unsaturated carboxylic acid and the raw material or solvent. Secondly, a new reaction route is presumed to proceed preferentially, wherein the compound (A) reacts with the raw material to produce an ester of the compound (A) and the resultant ester of the compound (A) is hydrolyzed and oxidized to produce the α,β-unsaturated carboxylic acid, and as a result, formation of by-products such as polymers, oligomers or esters can be suppressed.

In the present invention, it is preferable to further cause a carboxylic acid compound (B) having carbon number of 2 to 6 and having an acid dissociation exponent (pKa) of 4 or more to be present together with the compound (A) in the liquid phase. This improves the selectivity to the α,β-unsaturated carboxylic acid more.

The amount of the carboxylic acid compound (B) having carbon number of 2 to 6 to be added is preferably such an amount that a concentration of the compound (B) in the reaction solution becomes 1% by mass to 70% by mass. It is more preferably 2% by mass or more, particularly preferably 4% by mass or more. Further, it is preferably 60% by mass or less, particularly preferably 50% by mass or less.

Examples of the carboxylic acid compound (B) having carbon number of 2 to 6 and having an acid dissociation exponent (pKa) of 4 or more include acetic acid (pKa: 4.56), propionic acid (pKa: 4.67), n-butyric acid (pKa: 4.63), i-butyric acid (pKa: 4.63), n-valeric acid (pKa: 4.64), i-valeric acid (pKa: 4.58), n-hexanoic acid (pKa: 4.63), succinic acid (pKa: 4.00), glutaric acid (pKa: 4.13) and adipic acid (pKa: 4.26). Among them, any one of acetic acid, propionic acid, n-butyric acid, i-butyric acid and n-valeric acid is preferable, in particular, acetic acid is preferable. The carboxylic acid compound (B) may be used alone or in combination of two or more kinds. The carboxylic acid compound (B) does not include the α,β-unsaturated carboxylic acid which is the reaction product.

As the noble metal-containing catalyst to be used in the present invention, those on the market or those produced by contacting a compound containing a noble metal with a reducing agent can be used. When the noble metal-containing catalyst on the market is used, it is preferred to activate it by contacting it with a reducing agent previous to use it in a reaction.

The noble metal contained in the noble metal-containing catalyst to be used in the present invention is any one of palladium, platinum, rhodium, ruthenium, iridium, gold, silver and osmium, and among them, any one of palladium, platinum, rhodium, ruthenium, iridium and gold is preferable, in particular, palladium is preferable. Two or more kinds of these noble metals may be contained in the catalyst. The noble metal-containing catalyst may contain metals other than noble metal.

Generally, the catalyst is used as a supported catalyst in which a catalyst component is supported on a carrier, however, it is not necessary to be a supported catalyst. Examples of the carrier include activated carbon, carbon black, silica, alumina, magnesia, calcia, titania and zirconia, and among them, activated carbon, silica or alumina is preferable. As for a specific surface area of the carrier, though it cannot be absolutely said because it differs depending on a kind of carrier and the like, in the case of activated carbon, it is preferably 100 $m^2/g$ or more, more preferably 300 $m^2/g$ or more, and also preferably 5,000 $m^2/g$ or less, more preferably 4,000 $m^2/g$ or less. As the specific surface area of the carrier becomes smaller, the catalyst having its effective components being supported nearer the surface can be produced. As the specific surface area of the carrier becomes larger, the catalyst having its effective components being supported in large amount can be produced.

In the case of a supported catalyst, the supported ratio of a noble metal to the carrier is preferably 0.1% by mass or more to the mass of the carrier before it is supported, more preferably 0.5% by mass or more, furthermore preferably 1% by mass or more, and also preferably 40% by mass or less, more preferably 30% by mass or less, furthermore preferably 20% by mass or less.

The method for producing a supported catalyst is not particularly limited, and, for example, liquid-phase reduction method in which a noble metal is supported on a carrier by dispersing a carrier in a solution of a noble metal compound followed by reducing it by adding a reducing agent to it, or gas-phase reduction method in which a noble metal is supported on a carrier by impregnating a carrier with a noble metal compound solution and drying it followed by reducing it in a reducing atmosphere can be listed. Among them, a liquid-phase reduction method is preferable. As a method for producing an unsupported catalyst, liquid-phase reduction method in which a reducing agent is added to a noble metal compound solution to reduce it is preferable as well. Hereinafter, a method for producing a catalyst by liquid-phase reduction method will be explained.

As the solvent to be used in the case of reduction in liquid phase, water is preferable, however, depending on solubility of a noble metal compound and a reducing agent and dispersibility of a carrier in the case of using the carrier, organic solvents such as alcohols which include ethanol, 1-propanol, 2-propanol, n-butanol and t-butanol; ketones which include acetone, methyl ethyl ketone, methyl isobutyl ketone and cyclohexanone; organic acids which include acetic acid, n-valeric acid and isovaleric acid; and hydrocarbons which include heptane, hexane and cyclohexane can be used alone or in combination of two or more kinds.

The noble metal compound to be used is not particularly limited, however, for example, chlorides, oxides, acetates, nitrates, sulfates, tetraammine complex or acetylacetonato complex of the noble metal is preferable, and chlorides, oxides, acetates, nitrates or sulfates of a noble metal is more preferable, and further, halides, acetates or nitrates of a noble metal is particularly preferable.

In the case of producing a supported catalyst, a carrier and a noble metal compound are added to the solvent in a desired order or simultaneously to prepare a noble metal compound solution with dispersed carrier. The concentration of the noble metal compound in this solution is preferably 0.1% by mass or more, more preferably 0.2% by mass or more, particularly preferably 0.5% by mass or more, and is preferably 20% by mass or less, more preferably 10% by mass or less, particularly preferably 7% by mass or less. Subsequently, a reducing agent is added to this dispersion to reduce the noble metal, to support the reduced noble metal on the carrier. In the case of producing-an unsupported catalyst, the concentration of the noble metal compound in the solution is preferably the same range as that in the case of the supported catalyst mentioned above.

The reducing agent to be used is not particularly limited, however, examples include hydrazine, formaldehyde, sodium borohydride, hydrogen, formic acid, formate, ethylene, propylene, 1-butene, 2-butene, isobutylene, 1,3-butadiene, 1-heptene, 2-heptene, 1-hexene, 2-hexene, cyclohexene, allyl alcohol, methallyl alcohol, acrolein and methacrolein. This reducing agent can be used alone or in combination of two or more kinds.

In the case that the reducing agent is gas, it is preferable to carry out reduction in a pressure device such as an autoclave to increase the solubility of the reducing agent into the solution. In this case, the inside of the pressure device is pressurized by the reducing agent. The pressure is generally from 0.1 to 1 MPa (gage pressure; hereinafter, pressure is expressed in gage pressure). It is preferable that the gas-phase portion in the pressure device is replaced by inert gas such as nitrogen previous to introducing the reducing agent.

In the case that the reducing agent is liquid, there is no limit on a device to carry out reduction of the noble metal and the reduction can be carried out by adding a reducing agent in a solution of a noble metal compound. In this case, the amount of the reducing agent to be used is not particularly limited, however, generally it is about 1 to 100 mols to 1 mol of the noble metal compound.

The reducing temperature and the reducing time are different depending on a noble metal compound to be used or a reducing agent. The reducing temperature is preferably $-5°$ C. or more, more preferably 15° C. or more and preferably 150° C. or less, more-preferably 80° C. or less. The reducing time is preferably 0.1 hour or more, more preferably 0.25 hour or more, particularly preferably 0.5 hour or more, and preferably 4 hours or less, more preferably 3 hours or less, particularly preferably 2 hours or less.

The supported catalyst in which the noble metal is supported on the carrier or the unsupported catalyst is separated after reduction. The method for separating the catalyst is not particularly limited and, for example, a method such as filtration and centrifugation can be used. The separated catalyst is properly dried. The method for drying is not particularly limited and various methods can be used.

The amount of the noble metal contained in the residual solvent after reduction is preferably 10 mg/l or less. This amount can be adjusted by a concentration of the noble metal compound before the reduction, a reducing condition or the like. The noble metal in the residual solvent after the separation of the catalyst can be detected and confirmed easily by adding a reducing agent such as hydrazine. Further, the amount of the noble metal in the residual solvent can be determined quantitatively with an elemental analysis such as ICP.

The catalyst may be activated previous to being used in the liquid-phase oxidation reaction. The method for activating the catalyst is not particularly limited and various methods can be used. As the method for activating the catalyst, a method in which the catalyst is heated under reducing atmosphere in a flow of hydrogen is normal.

The physical properties of the catalyst prepared can be confirmed with BET specific surface area measurement, XRD measurement, CO pulse adsorption measurement, TEM observation and the like.

In the next place, a method for producing an $\alpha,\beta$-unsaturated carboxylic acid through liquid-phase oxidation of an olefin or an $\alpha,\beta$-unsaturated aldehyde with molecular oxygen will be explained.

Examples of the raw olefin include propylene, isobutylene and 2-buten. Examples of the raw $\alpha,\beta$-unsaturated aldehyde include acrolein, methacrolein, crotonaldehyde ($\beta$-methylacrolein) and cinnamaldehyde ($\beta$-phenylacrolein).

In the case that an olefin is used as the raw material, the $\alpha,\beta$-unsaturated carboxylic acid to be produced has the same carbon skeleton as the original olefin. Further, in the case that an $\beta,\beta$-unsaturated aldehyde is used as the raw material, its aldehyde group changes into carboxyl group in the $\alpha,\beta$-unsaturated carboxylic acid to be produced.

The method for producing an $\alpha,\beta$-unsaturated carboxylic acid of the present invention is suitable for liquid-phase oxidation producing acrylic acid from propylene or acrolein and methacrylic acid from isobutylene or methacrolein.

The raw olefin or the raw $\alpha,\beta$-unsaturated aldehyde may contain a small amount of impurities such as a saturated hydrocarbon and/or a saturated lower aldehyde.

As the source of molecular oxygen to be used in the liquid-phase oxidation reaction, air is economical, and also pure oxygen or mixed gas of air and pure oxygen can be used. If necessary, mixed gas in which air or pure oxygen is diluted with nitrogen, carbon dioxide or water vapor can be used too.

The solvent to be used in the liquid-phase oxidation reaction is not particularly limited, and, for example, water; alcohols such as tertiary butanol and cyclohexanol; ketones such as acetone, methyl ethyl ketone and methyl isobutyl ketone; organic acid esters such as ethyl acetate and methyl propionate; hydrocarbons such as hexane, cyclohexane and toluene can be used. Among them, ketones having carbon number of 3 to 6 and tertiary butanol are preferable. The solvent can be used alone or mixture of two or more kinds. Further, in the case of using alcohols, ketones and organic acid esters, it is preferable to use them as a mixture with water. In this case, the amount of water is not particularly limited, however, it is preferably 2% by mass or more to the mass of the mixed solvent, more preferably 5% by mass or more, and preferably 70% by mass or less to the mass of the mixed solvent, more preferably 50% by mass or less. It is desirable that the solvent is homogeneous, while it can be used in a heterogeneous state.

Although the liquid-phase oxidation reaction may be carried out either in a continuous system or in a batch system, a continuous system is preferable for industry in view of productivity.

The amount to be used of the olefin or the $\alpha,\beta$-unsaturated aldehyde which is the raw material of the liquid-phase oxidation reaction is preferably 0.1 part by mass or more to 100 parts by mass of the solvent, and more preferably 0.5 part by mass or more; and preferably 20 parts by mass or less, and more preferably 10 parts by mass or less.

The amount to be used of the molecular oxygen is preferably 0.1 mol or more to 1 mol of the olefin or the $\alpha,\beta$-unsaturated aldehyde which is the raw material, more preferably 0.3 mol or more, and particularly preferably 0.5 mol or more; and 30 mols or less, more preferably 25 mols or less, and particularly preferably 20 mol or less.

The catalyst is generally used in a dispersed state in a reaction liquid in which liquid-phase oxidation is carried out, while it may be used in a fixed bed. The amount to be used of the catalyst is preferably 0.1 part by mass or more as the catalyst existing in the reactor to 100 parts by mass of solution existing in the reactor, more preferably 0.5 part by mass or more, and particularly preferably 1 part by mass or more; and preferably 30 parts by mass or less, more preferably 20 parts by mass or less, and particularly preferably 15 parts by mass or less.

The reaction temperature and the reaction pressure are properly set depending on the solvent and the raw materials to be used. The reaction temperature is preferably 30° C. or more, more preferably 50° C. or more, and preferably 200° C. or less, more preferably 150° C. or less. Further, the reaction pressure is preferably atmospheric pressure (0 MPa) or more, more preferably 2 MPa or more, and preferably 10 MPa or less, more preferably 7 MPa or less.

EXAMPLES

Hereinafter, the present invention is further concretely explained with reference to examples and comparative examples, however, the present invention is not limited to the examples. In the following examples and comparative examples, "part" means part by mass.

Analysis of a Raw Material and a Product

Analysis of a raw material and a product was carried out by using gas chromatography. The conversion of an olefin or an α,β-unsaturated aldehyde, the selectivity to an α,β-unsaturated aldehyde to be produced and the selectivity to an α,β-unsaturated carboxylic acid to be produced are defined as follows:

The conversion (%) of an olefin or an α,β-unsaturated aldehyde=(B/A)×100;

The selectivity (%) to an α,β-unsaturated aldehyde=(C/B)×100; and

The selectivity to an α,β-unsaturated carboxylic acid (%)=(D/B)×100.

In the above formulae, A represents mol number of an olefin or an α,β-unsaturated aldehyde supplied; B represents mol number of an olefin or an α,β-unsaturated aldehyde reacted; C represents mol number of an α,β-unsaturated aldehyde produced; and D represents mol number of an α,β-unsaturated carboxylic acid produced. Further, in the case of oxidation reaction of an α,β-unsaturated aldehyde, C/B is 0.

The following examples and comparative examples demonstrate the reaction of producing methacrylic acid from isobutylene, wherein A represents the mol number of isobutylene supplied, B represents the mol number of isobutylene reacted, C represents the mol number of methacrolein produced and D represents the mol number of methacrylic acid produced.

Example 1

(Preparation of Catalyst)

To 60 parts of 85% by mass acetic acid aqueous solution, 1.1 parts of palladium acetate was dissolved under heating and the resultant solution was introduced into an autoclave with the internal volume of 150 ml together with 5.0 parts of activated carbon powder (specific surface area; 840 m$^2$/g) and the autoclave was shut tight. While stirring was carried out at a rate of 500 revolutions per minute, the inside of the system was replaced by nitrogen by introducing nitrogen gas into the system to the system pressure of 0.8 MPa, three times. Then propylene was introduced into it to the system pressure of from atmospheric pressure to 0.6 MPa and the resultant system was heated to 70° C. and kept at the same temperature for 1 hour.

Then the system was cooled to the room temperature, the system pressure was lowered and the autoclave was opened. The resultant liquid was filtered under reduced pressure under a nitrogen flow and black powder was obtained, which was washed by 75% by mass acetone aqueous solution and black powder was finally obtained. At this time, a small amount of hydrazine monohydrate was added to the filtrate and it was confirmed that there was not found any deposition of palladium.

The black powder thus obtained was dried over night under a nitrogen flow and palladium metal-supported catalyst was obtained. The supported ratio of palladium of this catalyst was 10% by mass.

(Evaluation of Reaction)

To an autoclave having internal volume of 330 ml equipped with gas introduction port (hereinafter, expressed as a reactor), 100 parts of 75% by mass acetone aqueous solution was introduced as a reaction solvent, and also 5.5 parts of the above-mentioned catalyst and 200 ppm of p-methoxyphenol to the reaction solution as radical scavenger were added. Further, 3 parts of trifluoroacetic acid (pKa: 0.30) was added as a compound (A) and the reactor was shut tight. After that, 6.5 parts of liquefied isobutylene was introduced to it and stirring of the system was carried out at a rate of 1,000 revolutions per minute.

Then, the temperature of the system was raised and when it reached 90° C., nitrogen was introduced into the system to 2.4 MPa, and the inside was further pressurized to 4.8 MPa by air. With the progress of the reaction, the pressure in the reactor dropped. Every time when the internal pressure dropped by 0.1 MPa, oxygen gas was added to reach the internal pressure of 4.8 MPa, and the amount of oxygen gas equivalent to a total of 1.7 MPa (1.04 mols to 1 mol of isobutylene) was used. The system was stirred for 50 minutes (reaction time) under this condition. During this reaction time, the conversion of liquefied isobutylene was adjusted about 50%.

Then, the system was cooled to about 10° C. in ice-water bath and gaseous components were totally recovered while reducing the system pressure. The system was opened and a part of the reaction liquid was sampled and the catalyst was completely removed by using membrane filter (pore size: 0.5 μm). The reaction solution and gas recovered were quantitatively determined with gas chromatography.

As a result of ICP emission spectral analysis of the reaction solvent, elusion of palladium was not detected. The results of the evaluation are shown in Table 1.

Example 2

The same procedure as in Example 1 was carried out except that, in the evaluation of the reaction, 3 parts of chloroacetic acid (pKa: 2.68) was added as a compound (A) instead of 3 parts of trifluoroacetic acid and the reaction time was 60 minutes. The amount of oxygen gas used in the reaction was equivalent to 1.7 MPa (1.04 mols to 1 mol of isobutylene). The results of the evaluation are shown in Table 1.

Example 3

The same procedure as in Example 1 was carried out except that, in the evaluation of the reaction, 3 parts of formic acid (pKa: 3.55) was added as a compound (A) instead of 3 parts of trifluoroacetic acid and the reaction time was 60 minutes. The amount of oxygen gas used in the reaction was equivalent to 1.5 MPa (0.92 mols to 1 mol of isobutylene). The results of the evaluation are shown in Table 1.

Example 4

The same procedure as in Example 1 was carried out except that, in the evaluation of the reaction, the amount of 75% by mass acetone aqueous solution as a reaction solvent was reduced to 60 parts; 40 parts of acetic acid (pKa: 4.56) was added as a carboxylic acid compound (B); and the reaction time was 50 minutes. The amount of oxygen gas used in the reaction was equivalent to 1.7 MPa (1.04 mols to 1 mol of isobutylene). The results of the evaluation are shown in Table 1.

Example 5

The same procedure as in Example 1 was carried out except that, in the evaluation of the reaction, the amount of 75% by mass acetone aqueous solution as a reaction solvent was reduced to 80 parts; 20 parts of acetic acid (pKa: 4.56) was added as a carboxylic acid compound (B); and the reaction time was 45 minutes. The amount of oxygen gas used in the reaction was equivalent to 1.6 MPa (0.98 mols to 1 mol of isobutylene). The results of the evaluation are shown in Table 1.

Comparative Example 1

The same procedure as in Example 1 was carried out except that, in the evaluation of the reaction, trifluoroacetic acid as a compound (A) was not added and the reaction time was 80 minutes. The amount of oxygen gas used in the reaction was equivalent to 1.6 MPa (0.98 mols to 1 mol of isobutylene). The results of the evaluation are shown in Table 1.

Comparative Example 2

The same procedure as in Example 1 was carried out except that, in the evaluation of the reaction, 3 parts of acetic acid (pKa: 4.56) was added as a compound (B) instead of 3 parts of trifluoroacetic acid as a compound (A) and the reaction time was 65 minutes. The amount of oxygen gas used in the reaction was equivalent to 1.7 MPa (1.04 mols to 1 mol of isobutylene). The results of the evaluation are shown in Table 1.

Comparative Example 3

The same procedure as in Example 1 was carried out except that, in the evaluation of the reaction, the amount of 75% by mass acetone aqueous solution as a reaction solvent was reduced to 60 parts; 40 parts of acetic acid (pKa: 4.56) was added as a carboxylic acid compound (B); trifluoroacetic acid as a compound (A) was not added; and the reaction time was 70 minutes. The amount of oxygen gas used in the reaction was equivalent to 1.7 MPa (1.04 mols to 1 mol of isobutylene). The results of the evaluation are shown in Table 1.

TABLE 1

|  | Compound (A), concentration | Carboxylic acid compound (B), concentration | Reaction time (min) | Conversion of isobutylene (%) | Selectivity to methacrolein (%) | Selectivity to methacrylic acid (%) |
| --- | --- | --- | --- | --- | --- | --- |
| Ex. 1 | Trifluoroacetic acid, 2.9 mass % | — | 50 | 52.7 | 44.7 | 25.5 |
| Ex. 2 | Chloroacetic acid, 2.9 mass % | — | 60 | 54.8 | 43.3 | 23.0 |
| Ex. 3 | Formic acid, 2.9 mass % | — | 60 | 48.7 | 46.4 | 20.8 |
| Ex. 4 | Trifluoroacetic acid, 2.9 mass % | Acetic acid, 38.8 mass % | 50 | 53.6 | 40.2 | 30.7 |
| Ex. 5 | Trifluoroacetic acid, 2.9 mass % | Acetic acid, 19.4 mass % | 45 | 51.4 | 35.8 | 33.5 |
| Comp. Ex. 1 | — | — | 80 | 57.7 | 35.0 | 20.1 |
| Comp. Ex. 2 | — | Acetic acid, 2.9 mass % | 65 | 59.3 | 37.4 | 19.7 |
| Comp. Ex. 3 | — | Acetic acid, 38.8 mass % | 70 | 52.5 | 30.7 | 18.8 |

As mentioned above, it was found that, according to the present invention, an α,β-unsaturated carboxylic acid can be produced in higher selectivity.

What is claimed is:

1. A method for producing an α,β-unsaturated carboxylic acid from an olefin in liquid phase by using a noble metal-containing catalyst and by causing a carboxylic acid compound having an acid dissociation exponent (pKa) of less than 4 to be present in the liquid phase.

2. The method for producing an α,β-unsaturated carboxylic acid according to claim 1, further causing a carboxylic acid compound (B) having carbon number of 2 to 6 and having an acid dissociation exponent (pKa) of 4 or more to be present together with a carboxylic acid compound in the liquid phase.

3. The method for producing an α,β-unsaturated carboxylic acid according to claim 1, wherein the noble metal-containing catalyst comprises palladium.

4. The method for producing an α,β-unsaturated carboxylic acid according to claim 2, wherein the noble metal-containing catalyst comprises palladium.

5. The method for producing an α,β-unsaturated carboxylic acid according to claim 1, wherein molecular oxygen used in the reaction is obtained from air, pure oxygen or a mixture of air and pure molecular oxygen.

6. The method for producing an α,β-unsaturated carboxylic acid according to claim 1, wherein the reaction solution contains 0.01% to 30% by mass of a carboxylic acid compound.

7. The method for producing an α,β-unsaturated carboxylic acid according to claim 1, wherein the reaction solution contains 0.1% to 30% by mass of a carboxylic acid compound.

8. The method for producing an α,β-unsaturated carboxylic acid according to claim 1, wherein the reaction solution contains 0.5% to 30% by mass of a carboxylic acid compound.

9. The method for producing an α,β-unsaturated carboxylic acid according to claim 1, wherein a carboxylic acid compound is trifluoroacetic acid.

10. The method for producing an α,β-unsaturated carboxylic acid according to claim 2, wherein the reaction solution contains 1% to 70% by mass of the carboxylic acid compound (B).

11. The method for producing an α,β-unsaturated carboxylic acid according to claim 2, wherein the reaction solution contains 2% to 70% by mass of the carboxylic acid compound (B).

12. The method for producing an α,β-unsaturated carboxylic acid according to claim 2, wherein the reaction solution contains 4% to 70% by mass of the carboxylic acid compound (B).

* * * * *